United States Patent [19]
Makishima

[11] Patent Number: 5,213,309
[45] Date of Patent: May 25, 1993

[54] COUPLER FOR CONNECTING A SPECIMEN SAMPLING BOTTLE TO A SUPPLYING PIPE OF A PLANT

[75] Inventor: Reichi Makishima, Tokyo, Japan
[73] Assignee: Nitto Kohki Co., Ltd., Tokyo, Japan
[21] Appl. No.: 853,146
[22] Filed: Mar. 18, 1992

[30] Foreign Application Priority Data
Mar. 26, 1991 [JP] Japan .......................... 3-026755[U]

[51] Int. Cl.⁵ .............................................. F16L 37/38
[52] U.S. Cl. ............................ 251/149.6; 251/149.1; 141/346; 141/349
[58] Field of Search .................. 251/149, 149.1, 149.3, 251/149.6, 149.9; 137/614, 614.05, 614.06, 614.02, 614.04; 141/346, 348, 349, 385, 366

[56] References Cited
U.S. PATENT DOCUMENTS
2,504,569  4/1950  Murphy et al. ............ 137/614.04 X
4,200,121  4/1980  Walter et al. .................. 137/614.05
4,388,947  6/1983  Steuerwald ..................... 137/614.06

FOREIGN PATENT DOCUMENTS
WO8301605  5/1983  PCT Int'l Appl. .

Primary Examiner—Martin P. Schwadron
Assistant Examiner—Kevin L. Lee
Attorney, Agent, or Firm—Nixon & Vanderhye

[57] ABSTRACT

A coupler for sampling specimen comprises a socket having a central hole, a plug insertable in the central hole of the socket, formed therein with a fluid passage for communicating with the interior of the supplying pipe and having a fixed position at which the socket is fixed to said plug, and a valve provided in the plug, adapted to close the fluid passage at the fixed position and having a sampling position at which the valve opens the fluid passage.

12 Claims, 4 Drawing Sheets

COUPLER FOR CONNECTING A SPECIMEN SAMPLING BOTTLE TO A SUPPLYING PIPE OF A PLANT

BACKGROUND OF THE INVENTION

1. Field of the Invention

This invention relates to a coupler for connecting a specimen sampling bottle to a supplying pipe of a chemical plant or a medicine plant when the specimen is sampled from the supplying pipe, and for disengaging the specimen sampling bottle from the supplying pipe.

2. Description of the Related Art

Conventionally, specimens have generally been sampled by means of a system which consists of valves, branch tubes connected to the supplying pipe of a chemical or medicine plant by means of the valves and specimen sampling bottles connected to the respective branch valves. In this system, the valves must be opened and closed every time a specimen is sampled.

Since, however, the connection of the sampling bottles to, and the disconnection of the same from, the branch tubes, and the opening and closing of the valves are carried out manually, it takes a considerable amount of time to sample specimens at many branch tubes many times, and in addition, sampling must be carried out carefully when the specimen is a chemically corrosive solution.

SUMMARY OF THE INVENTION

The object of this invention is to provide a coupler for sampling specimens safely and with a high operational efficiency from the supplying pipe of a chemical or medicine plant.

In order to attain this object, a coupler for sampling specimens according to this invention comprises a socket having a central hole; a plug insertable in the central hole of the socket, formed in the plug with a fluid passage communicating with the interior of the supplying pipe and having a fixed position at which the socket is fixed to the plug; and a valve provided in the plug, adapted to close the fluid passage at the fixed position and having a sampling position at which the valve opens the fluid passage.

When the plug body is not pushed deep in the socket, the valve is closed to prevent fluid chemical substances or fluid medicines from leaking from the supplying pipe. Only when the plug body is pushed deepest into the socket body to a sample specimen, the valve opens and the chemical substance or medicine is dispensed from the supplying pipe to the specimen sampling bottles. This arrangement allows a specimen to be sampled rapidly and prevents the chemical substance or medicine from leaking.

DETAILED DESCRIPTION OF THE PREFERRED EMBODIMENTS

Figure 1:
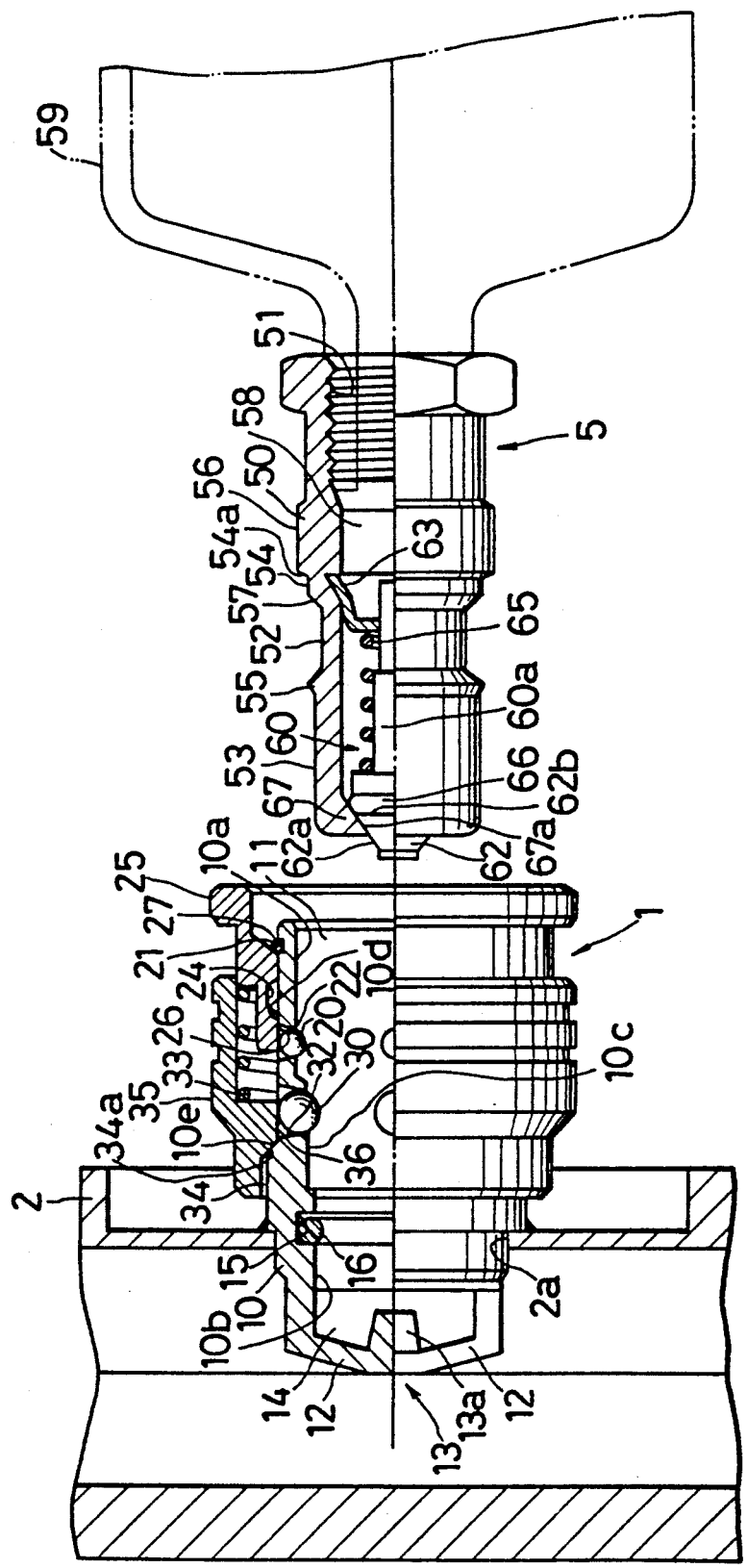
FIG. 1 is a side view of the first embodiment of the coupler according to this invention, in which a plug is not yet connected to a socket fixed to a supplying pipe, with the upper half shown in cross section.
Figure 2:
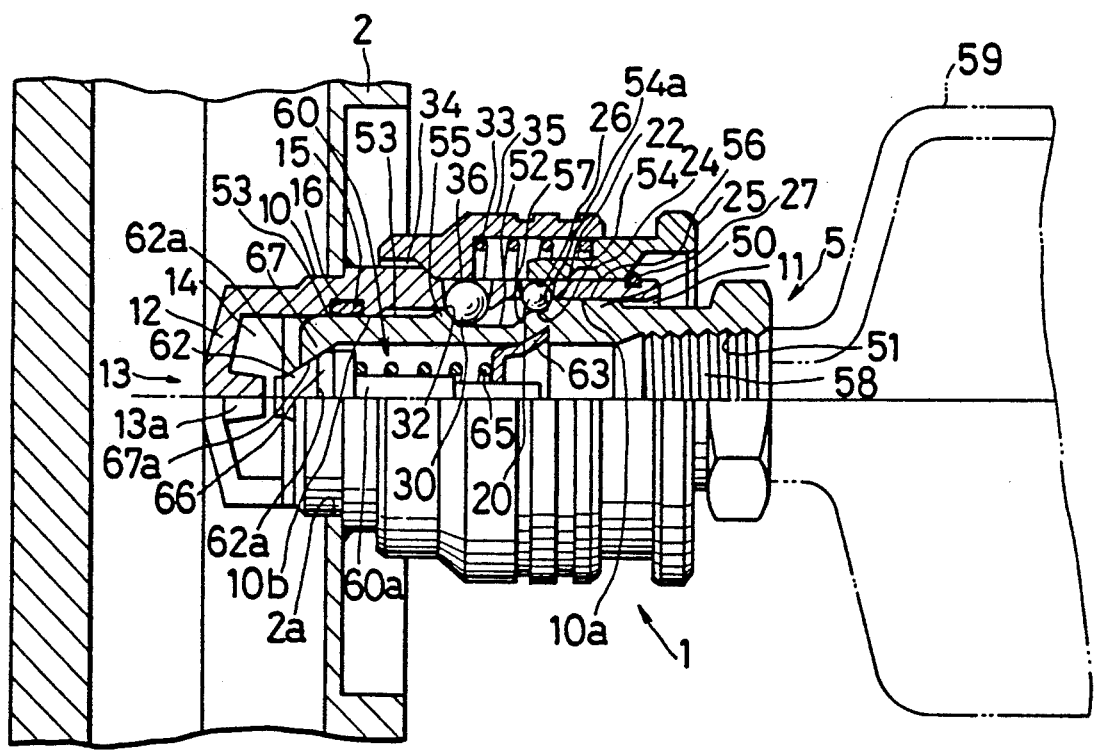
FIG. 2 is a side view of the first embodiment, in which the plug is connected to the socket, with the upper half shown in cross section.
Figure 3:
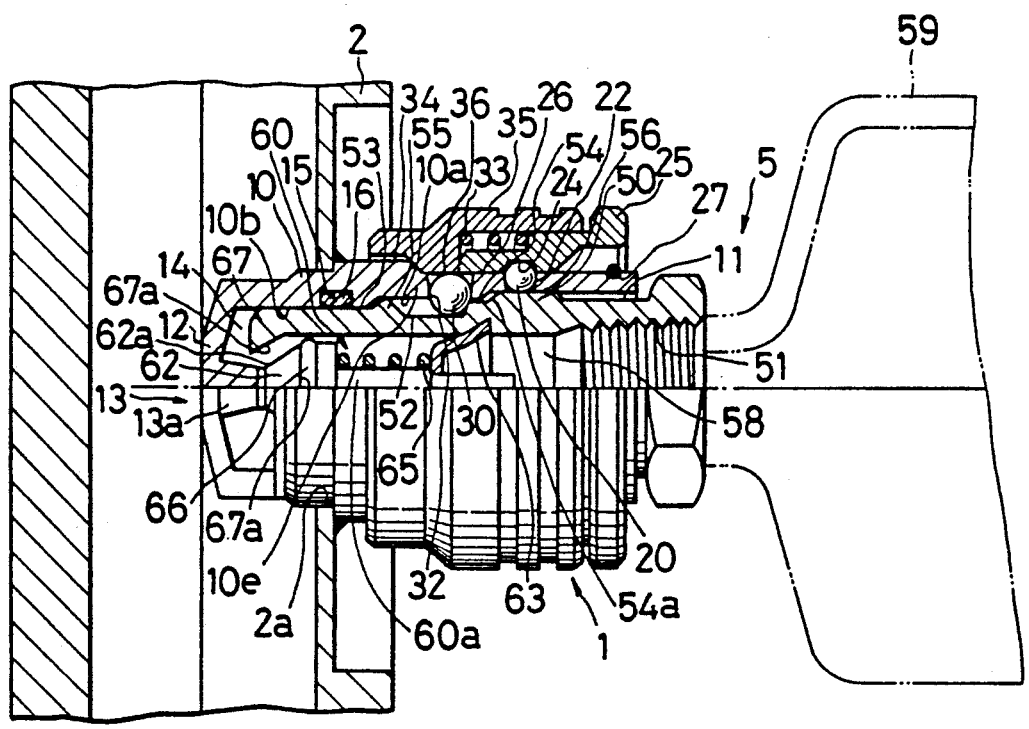
FIG. 3 is a side view of the first embodiment while in operation, with the upper half shown in cross section.

In FIGS. 1 to 3 is shown the first embodiment of a coupler according to this invention, which comprises a socket 1 and a plug 5. For simplicity, the end and end portion of each element comprising the plug 5 at which the plug 5 is inserted into the socket 1, and the end and end portion of each element comprising the socket 1 at which the socket 1 receives the plug 5, are referred to as the forward end and the forward end portion, respectively. Conversely, the other end and the other end portion of each of the elements of the plug 5 and the socket 1 are referred to as the rear end and the rear end portion, respectively.

As shown in FIG. 1, the socket 1 has a socket body 10 which comprises a forward inner peripheral wall 10a, a rear inner peripheral wall 10b having a diameter smaller than the forward peripheral wall 10a, and an intermediate inner peripheral wall 10c which has an intermediate diameter between both inner peripheral walls 10a and 10b and is continuous to both inner peripheral walls 10a and 10b. A generally cylindrical central hole 11 is defined by these inner peripheral walls 10a, 10b and 10c. A truncated conical valve pressing portion 13a is fixed by means of a pair of radially extending arms 12 to the rear end of the socket body 10 so as to be disposed at the center of the rear end of the socket body 10. The valve pressing portion 13a and the arms 12 constitute a valve pressing member 13 which exhibits an E shape when viewed sideways. Openings 14 are defined by the rear end of the socket body 10 and the valve pressing member 13. The rear end of the socket body 10 is perpendicularly connected at a connecting hole 2a to a portion of the peripheral wall of a supplying pipe 2 of a chemical or medicine plant, which supplying pipe conducts fluid chemical substance or medicine (hereinafter only referred to as "fluid chemicals"). The valve pressing member 13 extends along the main pipe 2 through the connecting hole 2a, and the openings 14 allow the central hole 11 to communicate with the interior of the supplying pipe 2. An annular groove 15 fitted by an O-ring 16 is formed in the rear inner peripheral wall 10b.

Formed circumferentially in the forward inner peripheral wall 10a are a plurality of (four, for example) tapered holes 22 in which rollable locking balls 20 (hereinafter referred to as the "first locking balls") are fitted so as to be movable in the radial direction of the socket body 10. On the forward half of the socket body 10 is mounted a first sleeve 25 having an intermediate portion formed with annular ball-receiving groove 24.

The first sleeve 25 has a rear inner peripheral wall 26 which is disposed behind the annular ball-receiving groove 24 and slidably contacts the forward outer peripheral wall 10d of the socket body 10. When the first sleeve 25 is rendered free as shown in FIGS. 1 and 2, the rear inner peripheral wall 26 contacts the first locking balls 20 and pushes them into the respective tapered holes 22. On the other hand, when the first sleeve 25 is pushed toward the supplying pipe 2 (hereinafter expressed as "retracts") and the annular ball-receiving groove 24 coincides with the tapered holes 22, the first locking balls 20 are received in the groove 24, as shown in FIG. 3. In the forward outer peripheral wall of the socket body 10 is formed an annular groove 21 in which is fitted a stop ring 27 for preventing the first sleeve 25 from slipping off. The rear end portion of the socket body 10 has an increased outer diameter.

A plurality of (four, for example) tapered holes 32 are formed circumferentially in the intermediate inner peripheral wall 10c of the socket body 10, and rollable locking balls 30 (hereinafter referred to as the "second locking balls") having a larger diameter than the first locking balls 20 are fitted in the tapered holes 32 so as to be movable in the radial direction of the socket body 10.

A second sleeve 35 has a reduced intermediate inner peripheral or ball holding inner wall 36 in slidable contact with the forward outer peripheral wall 10d of the socket body 10 such that the second sleeve 35 moves along the socket body 10. An annular ball-releasing recessed portion 34 is formed in the inner peripheral wall of the rear end portion of the second sleeve 35 so that the portion 34 receives the second locking balls 30 when the recessed portion 34 registers with the second locking balls 30. A compression coil spring 33 is provided between the first and second sleeves 25 and 35. By the urging force of the spring 33, the first sleeve 25 is abutted at its front inner edge against a stop ring 27 provided in the front portion of the outer peripheral wall of socket body 10, and the second sleeve 35 is abutted at the truncated conical face 34a of the ball-releasing recessed portion 34 against a truncated conical face 10e formed on the rear portion of the socket body 10, so that the state shown in FIGS. 1 and 2 can be maintained before and after the plug 5 is connected to the socket 1.

The plug 5 has a plug body 50 through and along which a generally cylindrical fluid passage 58 extends. In the rear end portion of the fluid passage 58 is formed a male screw 51 for engaging the mount of a specimen sampling bottle 59, which is shown by two-dot chain lines in FIGS. 1 to 4, with the plug body 50. The plug body 50 comprises a front cylindrical portion 53, a ball-engaging annular groove 52, a first annular shoulder 54 and a second annular shoulder 56, arranged in that order, from the front end toward the rear end of the plug 5. The front cylindrical portion 53 has the same outer diameter as the inner diameter of the rear inner peripheral wall 10b of the socket body 10. The ball-engaging annular groove 52 extends rearward from the rear end of the front cylindrical portion 53. An annular projection 55 is formed between the front cylindrical portion 53 and the ball-engaging annular groove 52. The groove 52 has a smaller diameter than the front cylindrical portion 53 and forms a wide groove. The first annular shoulder 54 has a larger diameter than the front cylindrical portion 53 and the annular groove 52. The second annular shoulder 56 has the same outer diameter as the inner diameter of the forward inner peripheral wall 10a of the socket body 10, which diameter is larger than that of the first annular shoulder 54. The annular groove 52 is provided at its rear side with a truncated conical wall face 57 continuous to the first shoulder 54, and a truncated conical wall face 54a is formed between both annular shoulders 54 and 56. The dispositions and dimensions of the annular groove 52, the annular shoulders 54 and 56 and the annular wall faces 57 and 54a are selected so as to satisfy conditions which will be described hereinafter. On the front end of the plug body 50 is formed a valve seat 67 having a triangular cross section and extending radially inward of the plug body 50. The inner face of the valve seat 67 makes a valve seat face 67a. An axially movable valve 60 is inserted in the fluid passage 58. The valve 60 comprises a valve head 62 having a truncated conical valve head face 62a complementary to the valve seat face 67a of the valve seat 67, and a valve rod 60a extending coaxially rearward from the valve head 62. An O-ring 66 is fitted in an annular groove 62b formed in the truncated conical valve head face 62a of the valve head 62, and a valve stop 63 having a shallow U-shaped cross section is fixed to the inner wall of an intermediate portion of the plug body 50 in the fluid passage 58. Between the rear end face of the valve head 62 and the valve stop 63 is provided a valve spring (a compression coil spring) 65 which surrounds the valve rod 60a. Before and after the plug 5 is connected to the socket 1 as shown in FIGS. 1 and 2, the spring 65 presses the valve head face 62a of the valve head 62 against the valve seat 67 through the O-ring 66, thereby preventing fluid chemicals from flowing from the interior of the supplying pipe 2 into the specimen sampling bottle 59 through the fluid passage 58.

The following is an explanation of how the plug 5 is to be connected to the socket 1, which is separately prepared as shown in FIG. 1.

First, the second sleeve 35 is manually retracted against the urging force of the compression coil spring 33, and the second locking balls 30 are relatively moved with respect to the second sleeve 35 from the region of the ball-holding inner wall 36 to the region of the ball-releasing recessed portion 34 so that the second locking balls 30 are rendered free. Thereafter the plug body 50 is inserted into the central hole 11 of the socket body 10.

The front cylindrical portion 53 of the plug body 50 passes by the first locking balls 20 and advances in contact therewith. After having passed beyond the annular projection 55, the tapered holes 32 of the socket body 10 are aligned radially with the annular groove 52 of the plug body 50, and at the same time, the first locking balls 20 engage the first annular shoulder 54 so that the plug body 50 cannot be further inserted into the socket body 10. When the second sleeve 35 is released, it is returned to the original position by the urging force of the compression coil spring 33. During the returning process, the second locking balls 30 move beyond the truncated conical face 34a and engage the ball holding inner wall 36 so as to be pressed against the annular groove 52. In this way, the plug 5 is connected to the socket 1 as shown in FIG. 2 to form a coupler which is ready for sampling. This position of the plug 5 in the socket 1 is expressed as the fixed position.

In this state, the O-ring 16 effects sealing between the rear inner peripheral wall 10b of the socket body 10 and the outer peripheral wall of the front cylindrical portion 53 of the plug body 50. Since the valve 60 continuously closes the fluid passage 58, the coupler comprising the socket 1 and the plug 5 functions as a blind plug for preventing fluid chemicals from leaking from the supplying pipe 2.

An explanation follows of how to sample fluid chemicals conducted through the supplying pipe 2.

First, a specimen sampling bottle 59 is screwed into the female screw 51 of the plug body 50. Then the first sleeve 25 is retracted against the urging force of the compression coil spring 33. The first locking balls 20 are received in the annular groove 24 and are rendered free. As the specimen sampling bottle 59 is pushed toward the supplying pipe 2, the plug body 50 advances with the rear inner peripheral wall 10b of the socket body 10 sealed by the O-ring 16, and at the same time, the first locking balls 20 are moved with respect to the plug body 50 from the first annular shoulder 54 to the second annular shoulder 56. Finally, the second locking balls 30 are abutted against the truncated conical wall face 57 of the annular groove 52 and the plug body 50 stops advancing. The position of the plug 5 in the socket 1 and of the valve 60 in the plug body 50 in this state is expressed as the sampling position.

In this state, as shown in FIG. 3, the valve head 62 of the valve 60 contacts the valve pressing portion 13a of the valve pressing member 13, and the valve 60 is retracted against the urging force of the valve spring 65 so as to open the fluid passage 58. While the specimen sampling bottle 59 is continuously pushed, fluid chemicals flow through the openings 14 and the fluid passage 58 into the specimen sampling bottle 59; i.e., sampling is carried out.

During the sampling process, the inner stepped portion of the second sleeve 35 is abutted against the rear end of the first sleeve 25 and thus does not advance further, so that the plug 5 is not accidentally removed from the socket 1.

As the pushing force of the specimen sampling bottle 59 is gradually reduced at the end of the sampling, the plug body 50 is slidably retracted, with sealing effected by means of the O-ring 16 between the inner peripheral wall of the socket body 10 and the outer peripheral wall of the plug body 50, and the O-ring 66 of the valve 60 contacts the valve seat 67 to close the fluid passage 58. The first locking balls 20 are moved with respect to the plug body 50 from the second annular shoulder 56 to the first annular shoulder 54, and the first sleeve 25 is returned to the original position by the urging force of the compression coil spring 33, as shown in FIG. 1.

After sampling, the second sleeve 35 is manually retracted against the urging force of the compression spring 33, and the second locking balls 30 are released from the ball holding inner wall 36 and received in the annular ball-releasing recessed portion 34. By doing so, the plug body 50 is easily removed from the socket body 10. Thereafter the socket 1 and the plug 5 are individually washed, using different washing processes.

Figure 4:
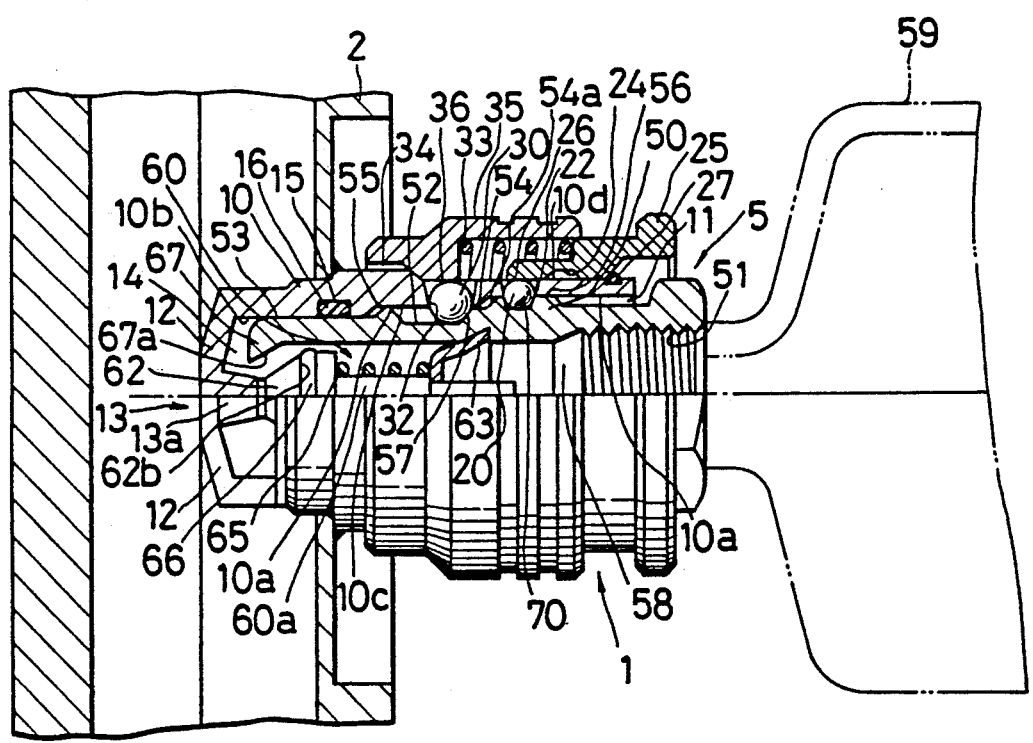
FIG. 4 is a side view of the second embodiment while in operation, with the upper half shown in cross section.

The second embodiment of the coupler according to this invention will be described with reference to FIG. 4, in which the fluid passage 58 of a plug body 50 is kept in an open state. This coupler has the same structure as the coupler of the first embodiment except that an annular groove 70 having the same diameter as the first annular shoulder 54 of the plug body 50 is formed in the annular step portion 56 of the plug body 50.

The connection of the plug 5 to, and the disconnection of the same from the socket 1 are carried out similarly to those of the first embodiment. However, when the specimen sampling bottle 59 is strongly pushed toward the supplying pipe 2 in order to sample fluid chemicals, the first locking balls 20 are neither received in the annular groove 24 of the second sleeve 25 nor disposed on the second annular shoulder 56 of the plug body 50, as in the case of the first embodiment as shown in FIG. 3. Rather, the first locking balls 20 are received in the annular groove 70 to release the first sleeve 25 and return the same to the original position by the urging force of the compression coil spring 33, as shown in FIG. 4, whereby the rear inner peripheral wall 26 of the first sleeve 25 presses first locking balls 20 against the annular groove 70 so as to lock the plug body 50 to the sleeve body 35.

With the second embodiment, therefore, the sampling operation is carried out without continuously manually pressing the specimen sampling bottle 59. After sampling, the first sleeve 25 is manually retracted against the urging force of the compression coil spring 33 and the first locking balls 20 are released. Then the plug body 50 advances by the urging force of the valve spring 65, with sealing effected by means of the O-ring 16 between the inner peripheral wall of the socket body 10 and the outer peripheral wall of the plug body 50. When the O-ring 66 of the valve 60 contacts the valve seat 67, the fluid passage 58 is closed. At the same time, the first locking balls 20 are moved with respect to the plug body 50 to the first annular shoulder 54, and the first sleeve 25 is returned to the original position by the urging force of the compression coil spring 33, as shown in FIG. 1.

What is claimed is:

1. A coupler for connecting a speciment sampling bottle to a supply pipe of a plant, said supply pipe having a lateral side formed with a connecting hole and also having an interior, said coupler comprising a socket and a plug,
   (1) said socket comprising:
      (I) a socket body having two open ends and comprising:
         (a) an outer peripheral wall;
         (b) a first inner wall portion at one of said open ends of said socket body and a second inner wall portion at the other open end of said socket body and an intermediate inner wall portion extending therebetween, said first, second and intermediate inner wall portions defining a central hole opening at said two open ends, said one open end of said socket body being connected to said supply pipe at said connecting hole thereof;
         (c) arm means crossing said one open end of said socket body, leaving, on both sides of said arm means, openings for communicating between said central hole and with said interior of said supply pipe;
         (d) a valve pressing member provided on said central portion of said arm means and extending therefrom towards the other open end of said socket body;
         (e) two rows of tapered holes formed circumferentially in said outer periphery of said socket body;
         (f) first locking balls fitted in one of said two rows of said tapered holes; and
         (g) second locking balls having a larger outer diameter than said first locking balls and fitted in the other row of said tapered holes;
      (II) a first sleeve mounted on said socket body and having an intermediate inner peripheral wall and an annular groove formed in said intermediate inner peripheral wall thereof;
      (III) a second sleeve mounted on said socket body and having an inner peripheral wall engageable with said second locking balls when said second sleeve is rendered free and a ball-releasing recessed portion at one end thereof for receiving said second locking balls when said second sleeve is moved toward said first sleeve; and;
      (IV) urging means provided between said first and second sleeves, for urging said first and said second sleeves for separating movement away from one another; and (2) said plug comprising:
(i) a plug body for insertion into said central hole of said socket body, and moveable when inserted into said plug body between a fixed position and a sampling position, said plug body comprising:
(a) an outer peripheral wall;
(b) a fluid passage extending through and along said plug body;
(c) an annular groove formed in said outer peripheral wall of said plug body for receiving said second locking balls when said plug body is at said fixed position;
(d) a first annular shoulder having an outer diameter larger than said annular groove of said plug body and formed on said outer peripheral wall of said plug body at a position at which said first annular shoulder receives said first locking balls when said plug body is at said fixed position;
(e) a first truncated conical wall face formed on said outer peripheral wall of said plug body so as to be continuous to said annular groove of said plug body and said first annular shoulder, for causing said second locking balls to abut against said first truncated conical wall face when said plug body is at said fixed position and for preventing said plug body from being further inserted into said socket body;
(f) a second annular shoulder having a larger diameter than said first annular shoulder and formed on said outer peripheral wall of said plug body so as to be disposed adjacent said first annular shoulder on a side thereof remote from said supplying pipe, for loading thereon said first locking balls with said first locking balls received in said annular groove of said first sleeve, when said plug body is at said sampling position; and
(g) a second truncated conical wall face formed on said outer peripheral wall of said plug body so as to be continuous to said first and second annular shoulders, for enabling said first locking balls to abut against said second truncated conical wall face and for preventing said plug body from being further inserted into said socket body; and
(ii) a valve movable in said fluid passage of said plug body, for closing said fluid passage when said plug body is at said fixed position and opening said passage when said plug body is at said sampling position.

2. The coupler according to claim 1, wherein said plug body has two ends, one end being disposed close to said supply pipe, and comprises a valve seat having a truncated conical valve seat face formed on said one end of said plug body and directed toward the other end of said plug body; said valve comprising a valve head and urging means for urging said valve head toward said valve seat such that said valve head engages said valve seat face with said valve head separated from said valve pressing member when said plug body is at said fixed portion and engages said valve pressing member with said valve head separated from said valve seat face when said plug body is at said sampling position.

3. The coupler according to claim 2, wherein said valve head has an outer peripheral wall provided with an O-ring pressed against said valve seat face providing a a hermetical seal when said valve head engages said valve seat face.

4. The coupler according to claim 2, wherein said valve has a valve rod extending from said valve head toward said other end of said plug body, and said urging means of said valve comprises a compression coil spring.

5. The coupler according to claim 4, wherein said compression coil spring has two ends, one end being more distant from said valve seat than the other end of said compression spring, said valve having a valve stop for holding said one end of said compression coil spring.

6. The coupler according to 1, wherein said annular groove of said plug body has two sides, one side being closer to said supply pipe than the other side, said plug body having an annular projection formed at said one side of said annular groove of said plug body.

7. The coupler according to claim 1, wherein said plug body is provided in said first annular shoulder with an annular groove for receiving said first locking balls when said plug body is at said sampling position.

8. The coupler according to claim 1, wherein said urging means comprises a compression coil spring.

9. The coupler according to claim 1, including an O-ring provided between said central hole of said socket body and said outer peripheral wall of said plug body upon insertion of said plug body into said socket body.

10. The coupler according to claim 1, wherein said socket body is provided in said outer peripheral wall thereof with a stop ring for preventing said first sleeve from slipping off said socket body.

11. The coupler according to claim 1, wherein said plug body has connecting means for connecting a specimen sampling bottle to said plug body.

12. The coupler according to claim 11, wherein said connecting means of said plug body comprises a female screw thread.

* * * * *